(12) United States Patent
Cordill

(10) Patent No.: US 6,862,916 B2
(45) Date of Patent: Mar. 8, 2005

(54) GAS CHROMATOGRAPH SAMPLE VALVE

(75) Inventor: Leroy David Cordill, Bartlesville, OK (US)

(73) Assignee: Siemens Energy & Automation, Inc., Alpharetta, GA (US)

( * ) Notice: Subject to any disclaimer, the term of this patent is extended or adjusted under 35 U.S.C. 154(b) by 0 days.

(21) Appl. No.: 10/443,511

(22) Filed: May 22, 2003

(65) Prior Publication Data

US 2003/0233863 A1 Dec. 25, 2003

Related U.S. Application Data

(60) Provisional application No. 60/385,488, filed on Jun. 4, 2002.

(51) Int. Cl.[7] .............................. G01N 30/04; F16K 7/00
(52) U.S. Cl. ........................ 73/23.42; 137/885; 251/331
(58) Field of Search ......................... 73/23.42; 137/865, 137/869, 885, 863; 251/331, 61.1

(56) References Cited

U.S. PATENT DOCUMENTS

| | | | | |
|---|---|---|---|---|
| 3,934,611 A | * | 1/1976 | Gachot et al. | 137/884 |
| 5,090,659 A | * | 2/1992 | Bronnert | 251/61.1 |
| 5,703,359 A | * | 12/1997 | Wampler, III | 250/288 |
| 5,775,371 A | * | 7/1998 | Pan et al. | 137/597 |
| 6,453,725 B1 | * | 9/2002 | Dahlgren et al. | 73/23.42 |
| 6,601,606 B2 | * | 8/2003 | Xu et al. | 137/341 |
| 6,715,733 B2 | * | 4/2004 | Wang et al. | 251/331 |
| 6,742,544 B2 | * | 6/2004 | Bergh et al. | 137/885 |

* cited by examiner

Primary Examiner—Michael Cygan

(57) ABSTRACT

The present invention is a sample valve for use in conjunction with a gas chromatograph. The sample valve design provides for both the inertness and low permeability performance of a diaphragm, and an elastomeric material to apply adequate sealing pressure to the diaphragm to seal with the mating surface of a center plate of the sample valve. This valve design allows the active sealing surface to be well polished without the previous concern for maintaining critical flatness of the mating surfaces of the machined parts.

9 Claims, 2 Drawing Sheets

GAS CHROMATOGRAPH SAMPLE VALVE

CROSS-REFERENCE TO RELATED APPLICATIONS

This application claims the benefit under 35 U.S.C. § 119(e) of U.S. Provisional Application No. 60/385,488 entitled "Simplified GC Sample Valve," filed on Jun. 4, 2002, which is herein incorporated by reference.

TECHNICAL FIELD

This invention relates generally to gas chromatographs. In particular, the invention pertains to sample valves for gas chromatographs.

BACKGROUND ART

Gas chromatography is a process typically used to separate volatile organic compounds. Gas chromatographs typically include ports for injection of the sample organic compounds attached to a chromatograph oven containing a column which separates the sample organic compound. Sample valves are generally used at the injection ports to precisely control and measure the samples to be injected.

The valves typically used in process gas chromatographs involve several precision machined parts. Most of the surfaces for these machined parts require some lapping to obtain a suitable flatness and then polishing to provide the necessary surface finish which will seal against a diaphragm material typically within the sample valve. The suitable polishing of machined surfaces of the valve must be performed for even the most simple air activated type valves, in which a diaphragm is the only moving part. In particular, in these valves the mating metal surfaces must be flat to provide the necessary sealing surface against the diaphragm. The diaphragm is usually made of Teflon®. Generally, the flatness required for the valves is approximately 2 lightbands over the surface of the diaphragm.

However, the more an item is polished, the more the desired flatness can be disrupted. Therefore a tradeoff is involved, and can result in a substantial cost incurred for each machined piece. Other prior art solutions for dealing with this tradeoff resulted in valve designs with larger tolerances for a less critical surface on the mating surfaces by utilizing an elastomeric type material for the diaphragm which provides the required sealing on the rougher surfaces. However, the diaphragm using elastomeric type materials allow more permeation of gases than Teflon diaphragms, or are not as inert. Depending on the application of the gas chromatograph, this can sometimes result in erroneous detection at the chromatograph oven.

Therefore there is a need for a sample valve for a chromatograph that is easier to manufacture and less costly.

SUMMARY OF THE INVENTION

According to one aspect of the invention, there is provided a valve apparatus for injecting a sample to be analyzed into a column of a gas chromatograph, said multiple valve apparatus comprising: an upper plate comprising at least one cavity for injecting activation gas and at least one recess for an elastomeric material, a first diaphragm disposed below said upper plate, a center plate disposed below said first diaphragm, said center plate having at least one port for injection of said sample, a second diaphragm disposed below said center plate, and a bottom plate comprising at least one cavity for injecting activation gas and at least one recess for an elastomeric material.

BRIEF DESCRIPTION OF THE FIGURES

The present invention will now be described with reference to the accompanying drawings wherein.

DETAILED DESCRIPTION OF THE FIGURES

The present invention provides a valve design which provides for both the inertness and low permeability performance of a diaphragm, and an elastomeric material to apply adequate sealing pressure to the diaphragm to seal with the mating surface of a center plate of the sample valve. Additionally, the elastomeric material is constrained to the small area needed to provide adequate pressure on the diaphragm. This allows the active sealing surface to be well polished without the previous concern for maintaining critical flatness of the mating surfaces of the machined parts.

The present invention additionally contains a means to contain the elastomeric material such that the elastomeric material can be thick enough to provide sufficient compression to accommodate the lack of flatness of the mating surface, while remaining in the correct position when activation pressure is applied.

In a preferred embodiment, an O-ring is used for the elastomeric material, and recesses are machined into the upper and bottom plates of the valve to position and contain the O-ring. This arrangement allows the upper and bottom plates to not require lapping or polishing of the mating surface. Also reduced is the flatness requirement on the mating surfaces of the center plate. This allows for much lower cost of valve construction.

In a preferred embodiment, Viton® material is used for the O-ring material. Viton® is a fluoroelastomer material available from E.I. Du Pont de Nemours and Company of Wilmington, Del. Viton® may be suitable at higher operating temperatures (up to 400° F.). It will be understood that other materials may also be suitable for the O-ring, particularly at lower temperatures (below 175° F.). Such materials may include either Buna-N® or Neoprene®.

In a preferred embodiment, Teflon® is used for the diaphragm material. Teflon® is a fluouropolymer material available from E.I. Du Pont de Nemours and Company of Wilmington, Del. It will be understood that other materials may be suitable for the composition of the diaphragm if suitable criterias of strength, inertness and flexibility are met.

Figure 1:
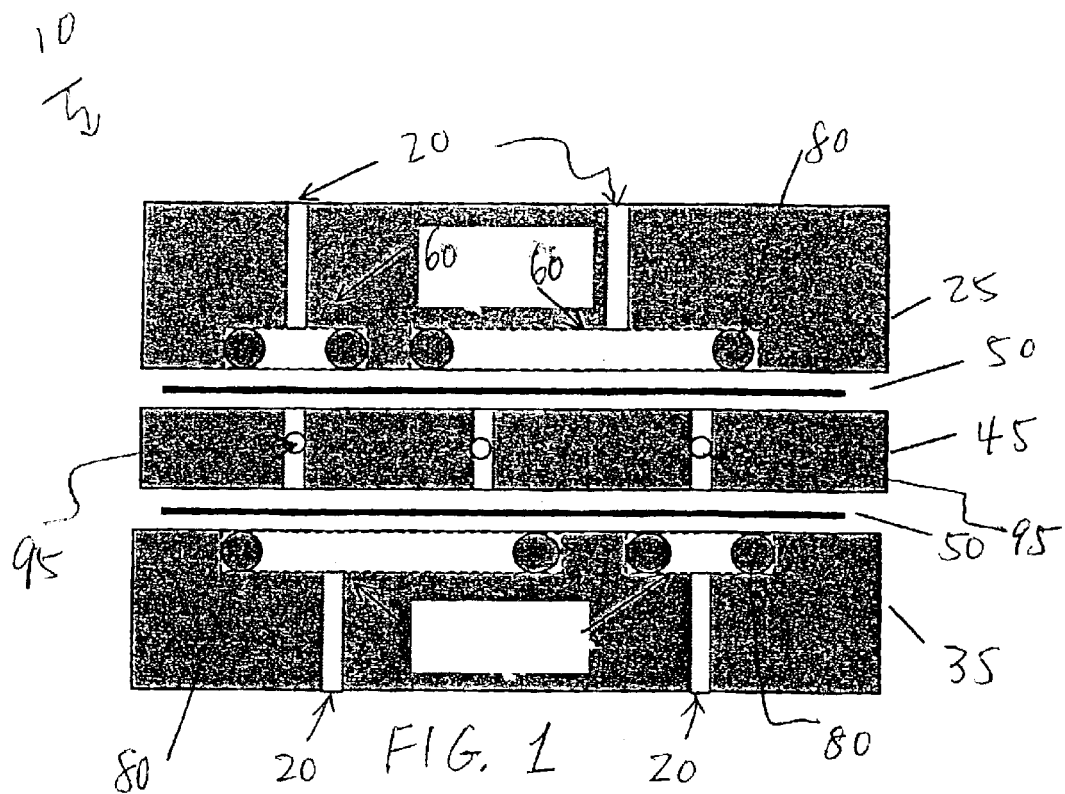
FIG. 1 is a schematic cross-section schematic diagram of an exemplary six port valve in accordance with the principles of the present invention.

Referring to FIG. 1, there is shown a schematic sectional view of a six port sample valve for use in process chromatographs in accordance with the principles of the invention. It will be understood that the apparatus described herein is not restricted to six port valves but will be applicable to any multiple port valve for process chromatographs. The sample valve 10 has cavities 20 for activation gas on the upper plate 25 and bottom plate 35. The cavities 20 are threaded ports which are bored through the upper plate 25 and the bottom plate 35 and connected through to recesses 60. The recesses 60 are configured for O-rings 80 (shown in cross-section) and are fabricated into the upper plate and bottom plate in a longitudinal slot shape. Disposed between the upper plate 25 and the center plate 45 is a diaphragm 50. The diaphragm 50 acts to seal against the polished surface of the center plate upon pressure from activation gas injected into cavities 20. Disposed between the center plate 45 and the bottom plate is a second diaphragm 50. The diaphragm 50 acts to seal against the polished surface of the center plate upon pressure from activation gas injected into cavities 20.

Figure 2:
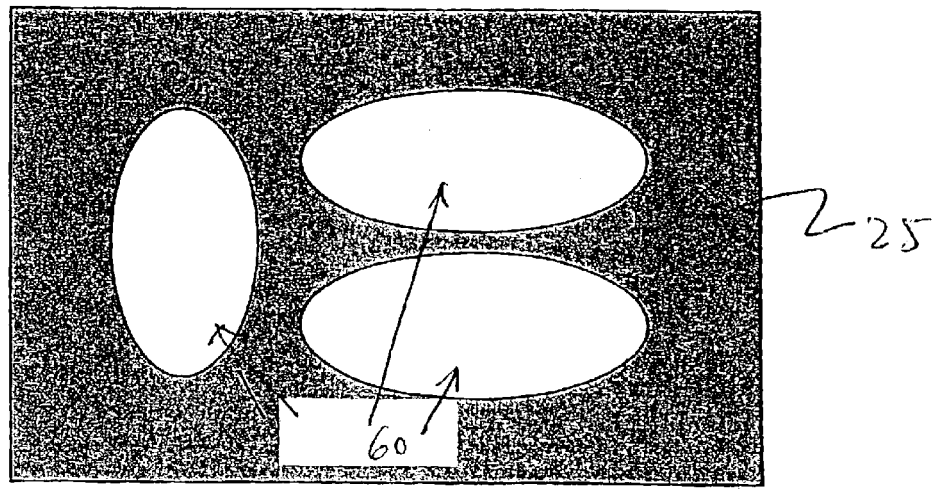
FIG. 2 is a schematic view of the upper plate of a sample valve in accordance with the principles of the present invention.

Referring to FIG. 2, there is shown a schematic view of the upper plate 25 of a sample valve in accordance with the principles of the present invention. The recesses 60 are generally in a slot shape.

Figure 3:
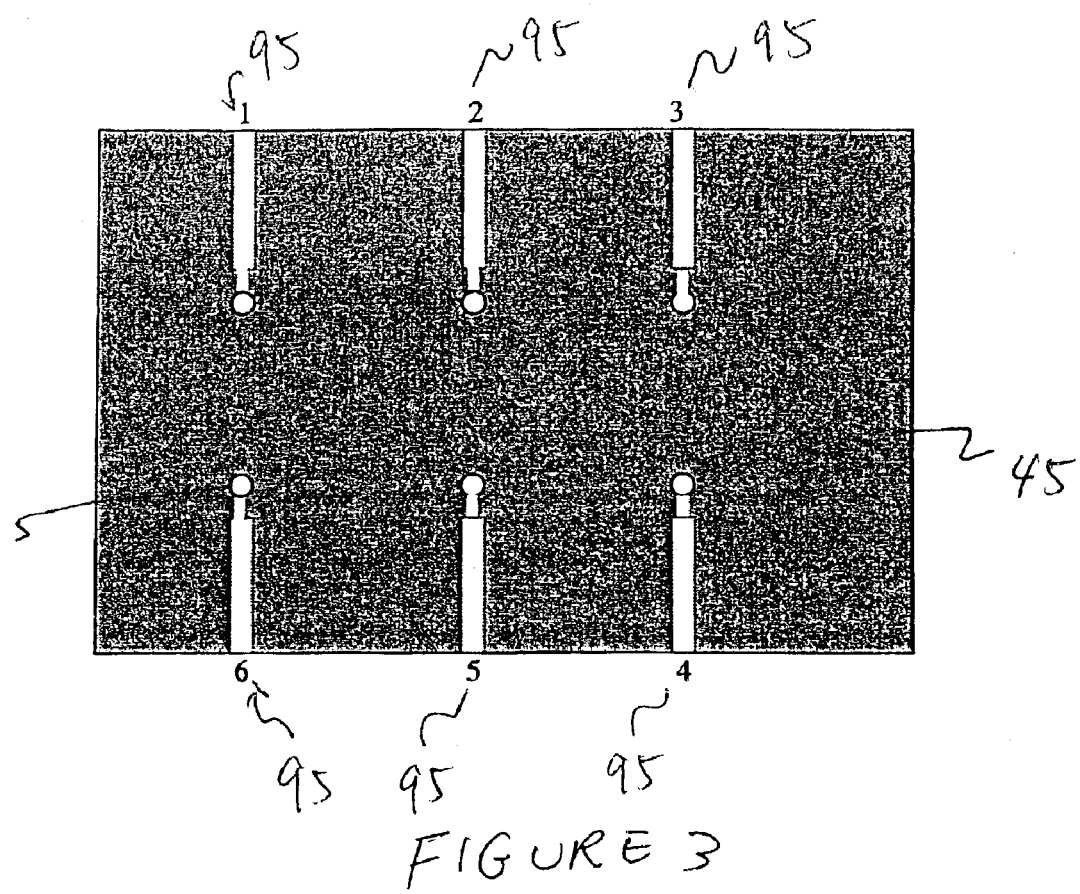
FIG. 3 is a schematic cross-section schematic diagram of the center plate of a sample valve in accordance with the principles of the present invention.

Referring to FIG. 3, there is shown a schematic view of the center plate 45 of a sample valve in accordance with the principles of the present invention. It will be understood that the illustrated sample valve is a six port valve, although the applicability of the invention to any multiport valve will be clear. The six ports 95 (labeled 1, 2, 3, 4, 5 and 6) are illustrated within the center plate 45.

Figure 4:
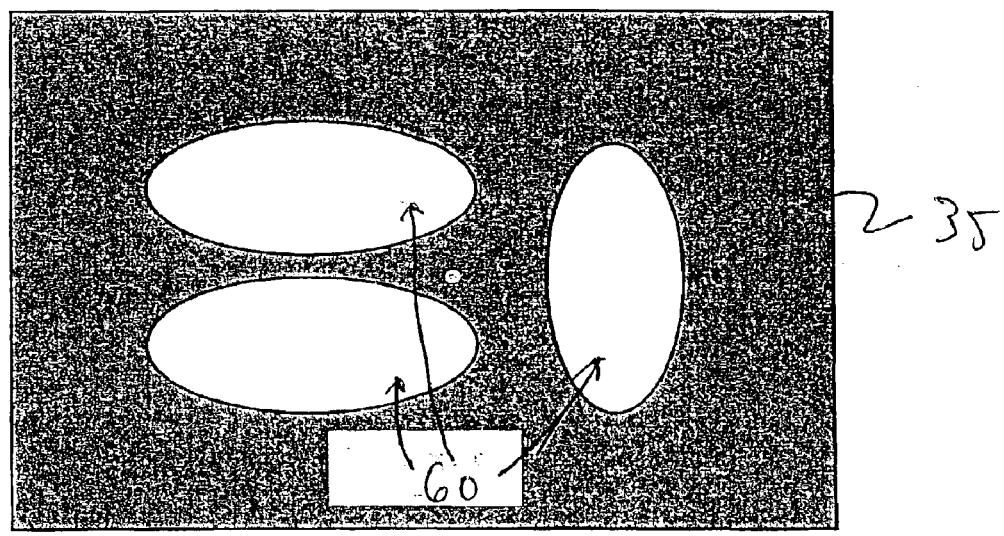
FIG. 4 is a schematic view of the bottom plate of a sample valve in accordance with the principles of the present invention.

Referring to FIG. 4, there is shown a schematic view of the bottom plate 35 of a sample valve in accordance with the principles of the present invention. The recesses 60 are generally in a slot shape.

In a preferred embodiment, the gas chromatograph of the present invention has a valve with a center plate which is comprised of ¼ inch thick center plate of aluminum. The preferred size of the center plate is 1 inch by 1.5 inches. The port passages are on a 0.3 inch c—c grid. The upper and bottom plates are ⅜ inch thick with O-ring recesses which are 0.250 inches wide and 0.525 inches long milled to a depth of 0.055 inches. In a preferred embodiment the O-rings are comprised of Viton® 011 size O-rings which are nominally 5/16 inches inside diameter, 7/16 inches outside diameter, and 1/16 inches cross-section. The diaphragm is 0.005 inches thick Teflon® PFA. The three plates are held together with four 8–32 bolts (not shown on the Figures).

The operation of the valve is illustrated herein. Activation gas is applied to all three upper plate cavities. In the alternative, all three lower plate cavities have activation gas applied. If activation gas is applied to all of the upper plate cavities, ports 1–2, 3–4, and 5–6 (shown in FIG. 3) can flow via the relaxed diaphragm in the bottom plate. Alternatively, if activation gas is applied to the bottom plate cavities, ports 1–6, 2–3 and 4–5 can flow via the relaxed diaphragm in the bottom plate.

It will be noted that the above relationship between the ports have been illustrated with respect to a six port valve. Those of ordinary skill in the art may readily determine the suitable port relationships for a multiport apparatus of six ports or any suitable number of ports.

It will be appreciated that the above described embodiments are illustrative and that those of ordinary skill in the art may readily devise their own implementations that incorporate the principles of the present invention and fall within the spirit and scope thereof.

What is claimed is:

1. A multiple valve apparatus for injecting a sample to be analyzed into a column of a gas chromatograph, said multiple valve apparatus comprising:

an upper plate comprising at least one cavity for injecting activation gas and at least one recess for an elastomeric material;

a first diaphragm disposed below said upper plate;

a center plate disposed below said first diaphragm, said center plate having at least one port for injection of said sample;

a second diaphragm disposed below said center plate; and a bottom plate comprising at least one cavity for injecting activation gas and at least one recess for an elastomeric material;

wherein said first at least one recess is aligned with a first O-ring;

wherein said second at least one recess is aligned with a second O-ring; and wherein the center plates comprises a thickness of about 0.25 inches and wherein the center plate comprises aluminum.

2. The multiple valve apparatus of claim 1, wherein the number of said ports of said center plate are six.

3. The multiple valve apparatus of claim 1, wherein the number of said ports of said center plate are ten.

4. The multiple valve apparatus of claims 1, wherein the first O-ring is made of Viton®.

5. The multiple valve apparatus of claim 1, wherein the second O-ring is made of Viton®.

6. The multiple valve apparatus of claim 1, wherein said first diaphragm is made of Teflon®.

7. The multiple valve apparatus of claim 1, wherein said second diaphragm is made of Teflon®.

8. The multiple valve apparatus of claim 1, wherein the upper plate comprises a thickness of about ⅜ inch.

9. The multiple valve apparatus of claim 1, wherein the bottom plate comprises a thickness of about ⅜ inch.

* * * * *